United States Patent [19]

Henssge et al.

[11] Patent Number: 5,047,060
[45] Date of Patent: Sep. 10, 1991

[54] FEMORAL BONE-HIP JOINT ENDOPROSTHESIS

[75] Inventors: Ernst J. Henssge; Wolfgang Köller; Pavel Dufek, all of Lübeck; Jorg Scholz, Berlin, all of Fed. Rep. of Germany

[73] Assignee: S+G Implants GmbH

[21] Appl. No.: 592,222

[22] Filed: Oct. 3, 1990

[30] Foreign Application Priority Data

Oct. 4, 1989 [EP] European Pat. Off. ........ 89118369.1

[51] Int. Cl.⁵ .......................... A61F 2/36; A61F 2/32
[52] U.S. Cl. ........................................ 623/23; 623/22
[58] Field of Search ........................ 623/23, 22, 18, 16

[56] References Cited

U.S. PATENT DOCUMENTS

| | | | |
|---|---|---|---|
| 4,051,559 | 10/1977 | Pifferi | 623/22 |
| 4,287,617 | 9/1981 | Tornier | 623/23 |
| 4,608,055 | 8/1986 | Morrey et al. | 623/23 |
| 4,718,914 | 1/1988 | Frey et al. | 623/22 X |
| 4,822,370 | 4/1989 | Schelhas | 623/23 |
| 4,957,510 | 9/1990 | Cremascoli | 623/23 |

FOREIGN PATENT DOCUMENTS 0201407  11/1986  European Pat. Off. ............. 623/23

Primary Examiner—Ronald Frinks
Attorney, Agent, or Firm—Toren, McGeady & Associates

[57] ABSTRACT

The femoral bone-hip joint endoprosthesis is characterized by the cavity construction of the prosthesis shank (10), by the ovaloid-conical aperture of the prosthesis shank and by the ovaloid-conical aperture of the upper prosthesis shank end for the accommodation of a cone plug connection (20).

2 Claims, 5 Drawing Sheets

FEMORAL BONE-HIP JOINT ENDOPROSTHESIS

BACKGROUND OF THE INVENTION

The present invention relates to a femoral bone-hip joint endoprosthesis with an anatomically shaped shank that tapers off conically in the direction of one of its ends and with an articular spheroid for an articular fossa retained on the latter.

The known hip joint prostheses are solidly forged or cast and, for this reason, depending on the specific weight of the materials employed, possess a relatively heavy weight. Such hip joint prostheses comprise a shank to be introduced into the medullar cavity of the femoral bone and a collar portion upon which a head portion is either mounted or welded.

SUMMARY OF THE INVENTION

The invention is based on the technical problem of providing a femoral bone-hip joint endoprosthesis without a collar portion and of light weight, but with a great variability in the choice of mounting or inserting connecting means for the head or the articular spheroid.

This technical problem is solved by the features stated in the claims 1 and 2.

In such an endoprosthesis constructed according to the invention, the otherwise well-known collar portion is dispensed with entirely; the endoprosthesis renders possible a wide variability in the choice of the inserting or mounting connecting means. The surgeon anchors the endoprosthesis in the femoral shank in such a way that the upper end of the endoprosthesis rests against the resection surface of the bone and subsequently renders possible any coupling whatever with different double cone plug connections. Both in the case of the first operation as well as in the case of possible subsequent operations for inspection purposes, the separation of shank and collar of a hip joint endoprosthesis realized by this endoprosthesis represents a great gain for the operating surgeon. Interventions for the replacement of a component are thus significantly facilitated.

The external form of the endoprosthesis corresponds to the known adapted shapes; it may be constructed so as to be smooth or be provided with a textured surface.

By means of the internal cavity construction within the upper area of the shank of the endoprosthesis it is achieved that the same has a lower weight when compared with the known prostheses. The endoprosthesis becomes lighter weight-wise, it is thereby adapted to the light construction of the bone. Variously constructed double cone connections are insertable through the oval-conical aperture of the retaining stud of the shank, that is to say that the use of double cones having differing lengths and diameters is possible and is simplified. Due to the oval configuration of the internal cross-section of the retaining stud and of the double cone of the plug connection, unintentional distortions of mounted or inserted double cones during the implantation are rendered impossible. To this is added the circumstance that, on account of the hollow chamber construction in the upper end of the endoprosthesis shank and by the insertion of the retaining stud for the double cone into the cavity of the shank, a high degree of elasticity is obtained without the strength of the shank being diminished within its upper area.

BRIEF DESCRIPTION OF THE DRAWINGS

In the following, embodiments of the invention are explained with the aid of the drawings. Thus

DETAILED DESCRIPTION OF THE PREFERRED EMBODIMENT

Figure 1:
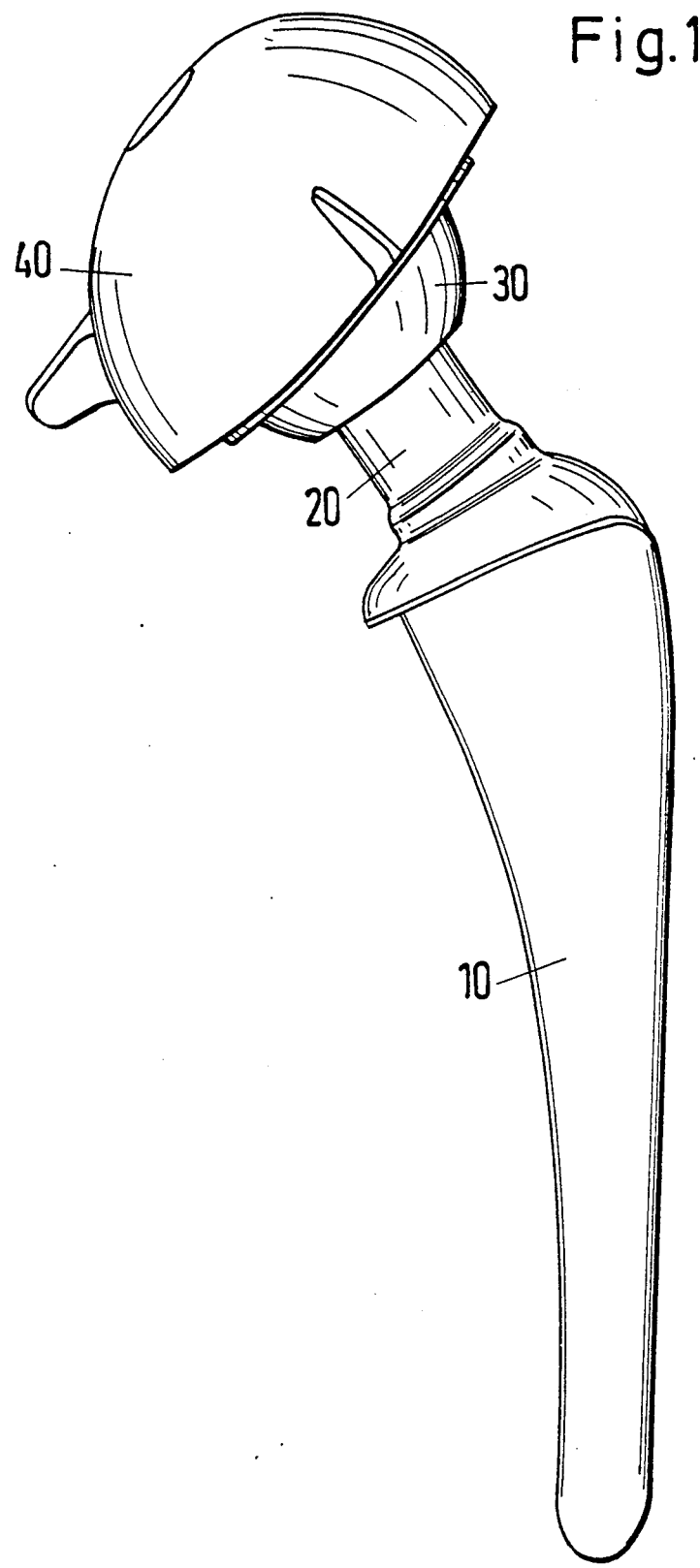
FIG. 1 shows a front view of a hip joint endoprosthesis.

The femoral bone-hip joint endoprosthesis comprises a shank 10, an articular spheroid 30 and an articular fossa 40, in which the articular spheroid is connected to the shank 10 by means of a double cone plug connection 20. In the FIGS. 2, 3 and 4, a femoral shaft, into which the shank 10 with the endoprosthesis is implanted, is identified with F.

In the upper end 10a of the shank 10, a cavity 11 is constructed in the same which, depending on the respective selected anatomical shape of the shank 10, possesses an appropriate form and suitable dimensions. If possible, this cavity 11 should extend as far into the shank 10 as possible, however, without the strength of the shank being in any way impaired or diminished thereby.

Figure 2:
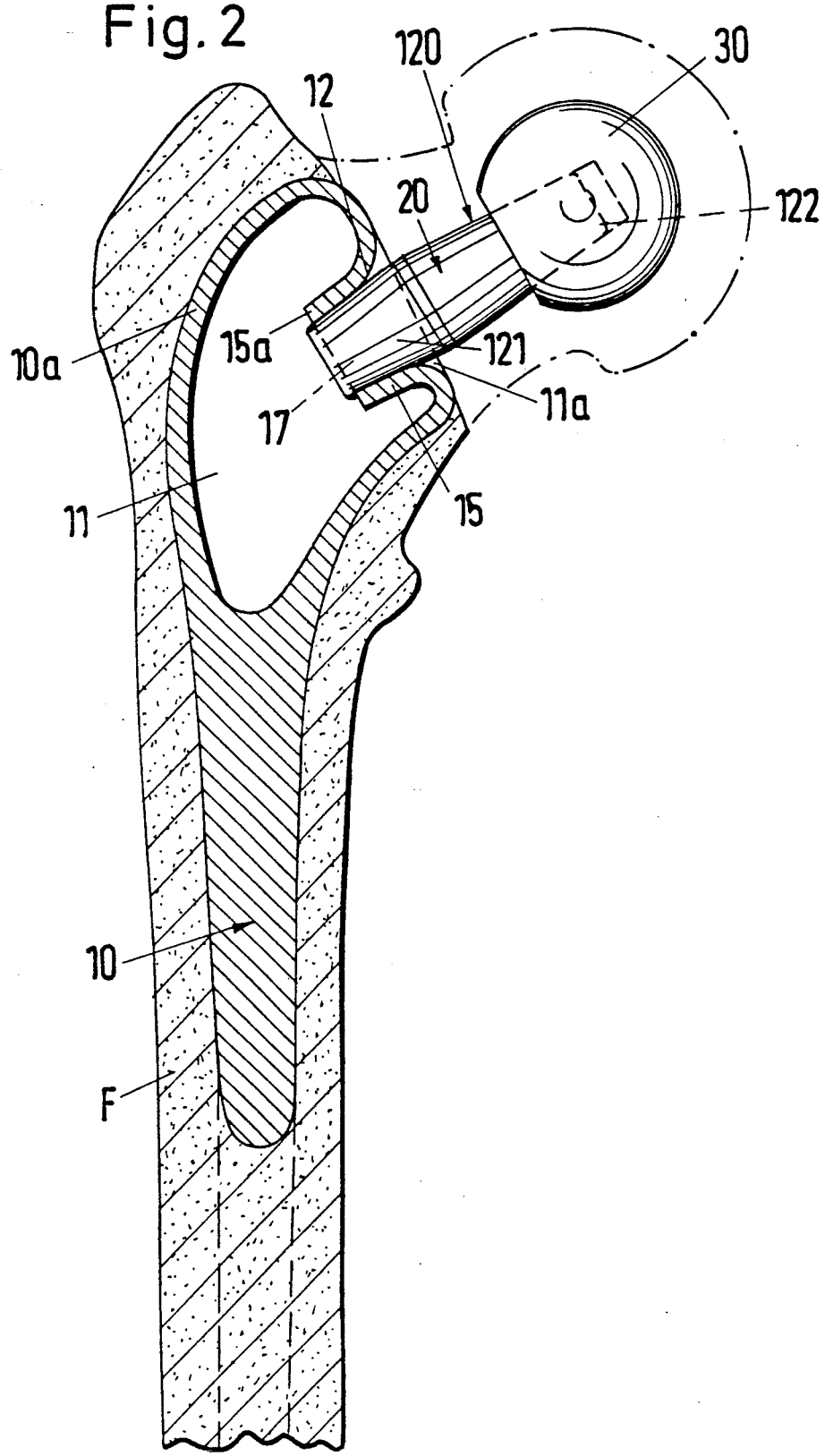
FIG. 2 shows a vertical longitudinal section through a femoral shaft with inserted shank fitted with a double cone plug connection.
Figure 3:
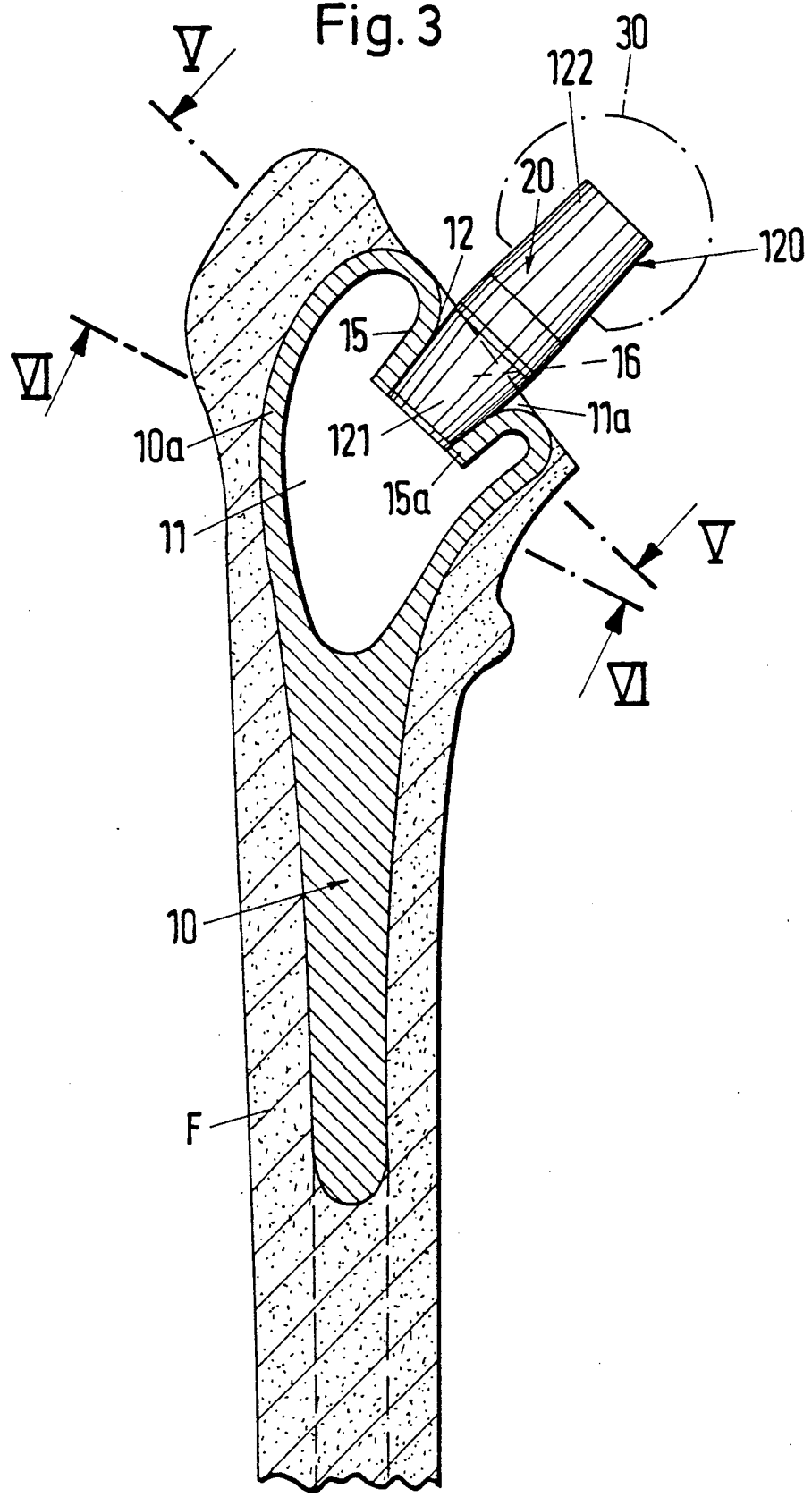
FIG. 3 shows a longitudinal section of a shank inserted into a femoral shaft fitted with a double cone plug connection having a shorter length than that of the shank per FIG. 2.
Figure 4:
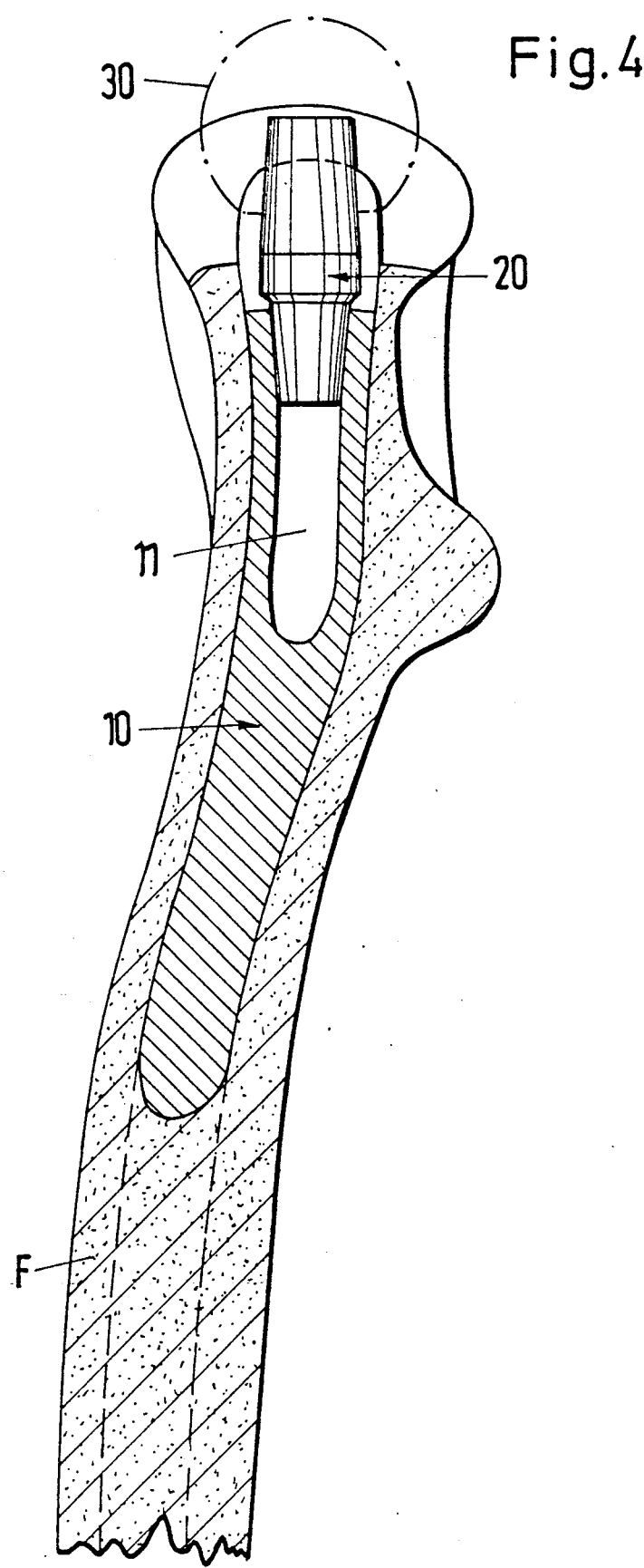
FIG. 4 shows a side view of FIG. 3.

The circumferential rim 12 of the shank 10 delimiting the upper cavity aperture 11a of cavity 11 is inserted into the cavity 11 while forming a collar-like and tubular retaining stud (15) (FIGS. 2, 3 and 4). In this case the length of the retaining stud 15 is selected in such a way that a firm fit of a double cone 120 of a plug connection 20 inserted into the retaining stud 15 is ensured without any internal cavity space being lost in the process or the stability of the wall delimiting the cavity being impaired.

The retaining stud 15, which serves to accommodate the double cone 120, according to an embodiment of the invention, possesses an internal cavity 17 which extends conically toward its free end 15a, so that the retaining stud 15 may be provided with an outer profile which is constructed in any way whatever or which possesses an outer wall shape constructed in any way whatever in order to, by way of example, so as to enable an additional support of the retaining stud 15 to be effected relative to the inner wall area delimiting the cavity 11.

Figure 5:
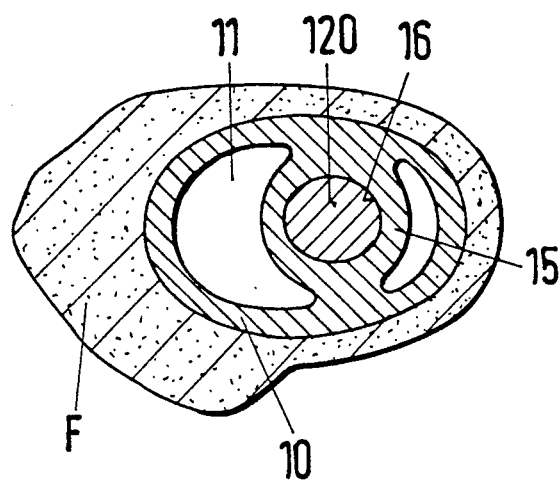
FIG. 5 shows a horizontal section in the direction of line V—V in FIG. 3.
Figure 6:
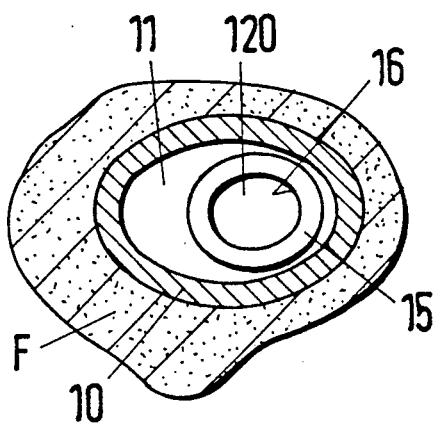
FIG. 6 shows a horizontal section in the direction of line VI—VI in FIG. 3.

Furthermore, the retaining stud 15 possesses an oval internal cross-section which is identified with 16 in FIGS. 5 and 6. The double cone 120, too, exhibits, at least within its terminal retaining stud insertion area 121, a shape and, more particularly, a cross-sectional configuration, which corresponds to the internal cross-sectional configuration of the retaining stud 15, so that the double cone 120 likewise has an oval cross-sectional configuration. The respective other end 122 which serves to accommodate the articular spheroid 30, likewise exhibits an oval cross-sectional configuration, however, also other cross-sectional configurations are possible, in which case such cross-sectional configurations have to be selected in each instance which correspond to the cross-sectional configuration of the cone insertion aperture in the articular spheroid 30.

According to a further embodiment of the invention, the tubular retaining stud 15 inserted into the cavity 11 of the shank 10, while the wall thickness extending over the entire length of the retaining stud 15 is maintained so as to be uniform, tapers off conically in the direction of its free end 15a (FIGS. 2, 3 and 4). Due to this design, a high degree of elasticity of the retaining stud 15 relative to the delimitation wall of the cavity 11 is achieved.

What is claimed is:

1. Femoral bone-hip joint endoprosthesis with an anatomically shaped shank (10) tapering conically in the direction of one of its ends and with an articular spheroid (30) secured to the same for an articular fossa (40), characterized in that, in the upper end (10a) of the shank (10) facing the articular spheroid, a cavity (11) is constructed, and in that the circumferential rim (12) delimiting the upper cavity aperture (11a), while forming a collar-like and tubular retaining stud (15), is inserted into the cavity (11), while the retaining stud (15) possesses an internal cavity (17) which tapers conically toward its free end (15a) and an oval internal cross-section (16) for accommodating a double cone plug connection (20), the double cone (120) of which, at least within the area of the retaining stud (15), is provided with a cross-sectional configuration that corresponds to the internal cross-sectional configuration of the latter.

2. Femoral bone-hip joint endoprosthesis with an anatomically shaped shank (10) tapering off conically in the direction of one of its ends with an articular spheroid (30) secured to the same for an articular fossa (40), characterized in that, in the upper end (10a) of the shank (10), a cavity (11) is constructed, and in that the circumferential rim (12) delimiting the upper cavity aperture (11a), while forming a collar-like and tubular retaining stud (15), is inserted into the cavity (11), while the retaining stud (15) possesses a uniform wall thickness extending over the entire length of the retaining stud (15) and tapers off conically toward its free end (15a) and has an oval cross-section for accommodating a double cone plug connection (20), the double cone (120) of which, at least within the area of the retaining stud (15), is provided with a cross-sectional configuration corresponding to the internal cross-sectional configuration of the latter.

* * * * *